US 8,419,271 B2
Apr. 16, 2013

(12) United States Patent
Huang et al.

(54) APPARATUS WITH TEMPERATURE SELF-COMPENSATION AND METHOD THEREOF

(75) Inventors: Long-Sun Huang, Taipei (TW); Yu-Fu Ku, Chiayi County (TW); Yi-Kuang Yen, Kaohsiung (TW); Shu Kuan, Keelung (TW); Kuang-Chong Wu, Taipei (TW); Shiming Lin, Taipei (TW); Ping-Yen Lin, Taipei (TW)

(73) Assignee: National Taiwan University, Taipei (TW)

( * ) Notice: Subject to any disclaimer, the term of this patent is extended or adjusted under 35 U.S.C. 154(b) by 401 days.

(21) Appl. No.: 12/789,289

(22) Filed: May 27, 2010

(65) Prior Publication Data

US 2011/0158288 A1    Jun. 30, 2011

(30) Foreign Application Priority Data

Dec. 29, 2009 (TW) .............................. 98145653 A

(51) Int. Cl.
  *G01K 7/16* (2006.01)
(52) U.S. Cl.
  USPC ........... 374/117; 374/185; 374/1; 374/E7.018
(58) Field of Classification Search ................ 374/1, 46, 374/52, 55, 117, 118, 119, 141, 185, 187, 374/198, 199; 73/765, 766, 768, 778
  See application file for complete search history.

(56) References Cited

U.S. PATENT DOCUMENTS

| 4,166,269 | A | * | 8/1979 | Stephens et al. | ................ | 338/3 |
| 4,419,598 | A | * | 12/1983 | Spitz et al. | ................... | 310/311 |
| 4,836,025 | A | * | 6/1989 | Mihara | .......................... | 73/497 |
| 5,138,414 | A | * | 8/1992 | Shinohara | ..................... | 257/417 |
| 5,511,427 | A | * | 4/1996 | Burns | ............................. | 73/708 |
| 6,002,963 | A | * | 12/1999 | Mouchawar et al. | .......... | 607/18 |
| 6,096,559 | A | * | 8/2000 | Thundat et al. | ............... | 436/147 |
| 6,100,524 | A | * | 8/2000 | Yagi et al. | ........................ | 850/53 |
| 6,966,231 | B2 | * | 11/2005 | Sheplak et al. | ................ | 73/861 |
| 7,340,960 | B2 | * | 3/2008 | Niblock | ........................ | 73/760 |
| 7,556,775 | B2 | * | 7/2009 | McGill et al. | ................... | 422/88 |
| 7,928,343 | B2 | * | 4/2011 | King et al. | ................ | 219/444.1 |
| 2003/0176850 | A1 | * | 9/2003 | Melvas | ........................ | 604/533 |
| 2007/0170814 | A1 | * | 7/2007 | Sykes et al. | .................... | 310/317 |
| 2009/0265819 | A1 | * | 10/2009 | Watanabe et al. | ............... | 850/21 |
| 2010/0095774 | A1 | * | 4/2010 | Sone et al. | ...................... | 73/580 |

FOREIGN PATENT DOCUMENTS

TW    200926203 A    6/2009

* cited by examiner

*Primary Examiner* — R. A. Smith

(57) ABSTRACT

A system for compensating a thermal effect is provided and includes a substrate structure and a microcantilever. The substrate structure includes a first piezoresistor. The first piezoresistor is buried in the substrate structure and has a first piezoresistance having a first relation to a first variable temperature. The microcantilever has the thermal effect and a second piezoresistance having a second relation to the first variable temperature, wherein the thermal effect is compensated based on the first and the second relations.

20 Claims, 8 Drawing Sheets

APPARATUS WITH TEMPERATURE SELF-COMPENSATION AND METHOD THEREOF

FIELD OF THE INVENTION

The present invention relates to an apparatus with temperature self-compensation and method thereof, and more particularly to a system and method for compensating a thermal effect of a piezoresistive sensor.

BACKGROUND OF THE INVENTION

In the recent years, the research in the biosensor vigorously proceeds because of the development of the nanotechnology, the miniaturization of the biochemical medical sensor and the demands on low concentration and high precision. Please refer to FIG. 1, which is a schematic diagram showing a conventional biosensor 10. The biosensor 10 includes an analyte layer 101, a biorecognition element layer 102 and a biotransducer 103. In general, the analytes in the analyte layer 101 is carried in the fluid 104 flowing to pass the biorecognition element layer 102. A mechanism is used to bind the analytes to the biorecognition element layer 102 for recognizing the analytes. The mechanism may be the configuration complementation between the antibody and the antigen, or at least one of the ionic bond, the hydrogen bond, the Van Der Waals' force and the hydrophobicity gravity between molecules. The configuration complementation may be the inter-binding mechanism between two protein molecules, that is, the shapes of the lock and the key must be complementary in order to bind them.

Please refer to Table 1, which is a table showing types of biosensors, and recognition mechanisms thereof. The biosensors may be classified as a direct bioaffinity biosensor and a biocatalytic sensor. The corresponding relations among the signal generating method, the bioaffinity-corresponding object and the analyte for the biosensors are shown in Table 1.

TABLE 1

| Sensor type | Signal generating method | Bioaffinity-corresponding object | Analyte |
|---|---|---|---|
| Direct bioaffinity biosensor | Directly generating bonding between the biorecognition element layer and the analyte layer | Enzyme | Substrate analogue |
| | | Antibody | Antigen Virus Cell |
| | | Nucleic acid | Complementary sequence |
| | | Lectin | Glycoprotein |
| Biocatalytic sensor | Transforming to generate metabolite | Chemical receptor | Target analyte |
| | | Apoenzyme | Prosthetic group |
| | | Enzyme | Inhibitor |
| | | Antibody | Enzyme-marked antigen |
| | Chemical transformation | Enzyme | Substrate |
| | | Organelle | Cofactor |
| | | Microbe | |

Types of biosensors may be classified as an optical type, an electrochemical type and a mechanical type according to the signal generating methods thereof. At present, the optical-type biosensor is widely used. However, it is uneasy to carry the optical-type biosensor because the volume thereof is too big.

The mechanical-type biosensor estimates the weight variation by measuring the resonance variation resulting from binding the analyte and the reactant. However, it is easy to result in bad sensitivity because of the influence of the structure on the mechanical-type biosensor itself. Therefore, the research focus is turned to the piezoresistive-type microcantilever.

The piezoresistive-type microcantilever mainly uses the influence of the stress on it to detect the analyte. When the analyte is absorbed on the piezoresistive-type microcantilever, the surface stress thereof can be changed because of the action force among the molecules, which causes the piezoresistive-type microcantilever to bend upward or downward, so that the piezoresistance thereof is changed. The action force among the molecules involves the mutual-absorption or the mutual-repulsion of the electrostatic force, the pushing effect resulting from the space limit among the molecules, the hydrophily/hydrophobicity change on the surface of the piezoresistive-type microcantilever, the configuration change of the absorbed biomolecules, and the change of the environmental solution.

The piezoresistive-type microcantilever includes a piezoresistor having a piezoresistance. The piezoresistive-type microcantilever has a disadvantage due to a resistance temperature coefficient effect and a bimorph effect both resulting from the temperature variation of the piezoresistive-type microcantilever or the environmental temperature variation. The resistance temperature coefficient effect results from that the resistance temperature coefficient of the piezoresistor itself is changed under the influence of the temperature variation of the piezoresistive-type microcantilever, and results in the variation of the piezoresistance thereof, and such the piezoresistance variation is known as the resistance temperature coefficient effect of the piezoresistive-type microcantilever. In general, the bimorph effect happens in a piezoresistive-type microcantilever including a plurality of layers made of a multilayer composite material, wherein the plurality of layers have different thermal expansion coefficients. When the environmental temperature or the temperature of the piezoresistive-type microcantilever varies, the differences among the expanded lengths of the plurality of layers result in that the piezoresistive-type microcantilever is acted under stress to bend upward or downward, which causes the variation of the piezoresistance thereof. The piezoresistance variation resulting from the temperature variation is the main reason resulting in an error, so that many methods to reduce the error are proposed.

Please refer to FIG. 2(a), which is a schematic diagram showing a conventional microcantilever sensing apparatus 20. The microcantilever sensing apparatus 20 includes a reference microcantilever 201, a sensing microcantilever 202 and a Wheatstone bridge 203. The Wheatstone bridge 203 includes resistors A1, A2, A3 and A4 respectively having resistances $R_1$, $R_2$, $R_3$ and $R_4$. The Wheatstone bridge 203 receives an input voltage $V_{IN}$. The voltage $V_{13}$ comes from distributing the input voltage $V_{IN}$ to the resistances $R_1$ and $R_3$. The voltage $V_{24}$ comes from distributing the input voltage $V_{IN}$ to the resistances $R_2$ and $R_4$. There is the voltage $V_{OUT}=V_{13}-V_{24}$.

The reference microcantilever 201 includes a reference resistor A21 serving as the resistor A2. The reference resistor A21 has a reference resistance R-ref; that is, the reference resistance R-ref is the resistance $R_2$. The sensing microcantilever 202 includes a sensing resistor A22 serving as the resistor A1. The sensing resistor A22 has a sensing resistance R-sensor; that is, the sensing resistance R-sensor is the resistance $R_1$. The variation of the reference resistance R-ref and that of the sensing resistance R-sensor are considered as follows. According to the voltage-dividing theorem, the voltage $V_{13}$ satisfies $V_{13}=V_{IN}\times R_3/(R_1+R_3)$ and the voltage $V_{24}$ satisfies $V_{24}=V_{IN}\times R_4/(R_2+R_4)$. Therefore, the voltage $V_{OUT}$ satisfies $V_{OUT}=V_{13}-V_{24}=V_{IN}\times[(R_3/(R_1+R_3))-(R_4/(R_2+R_4))]$. In one practical application, the resistances $R_1$, $R_2$, $R_3$ and $R_4$ satisfy $R_1=R_2=R_3=R_4=R$. When only the resistance $R_1$ has a tiny variation $\Delta R_1$, the voltage $V_{OUT}$ satisfies $V_{OUT}=V_{IN}\times[(R/(\Delta R_1+R+R))-(R/2R)]$. Therefore, the voltage $V_{OUT}$ satisfies $V_{OUT}\approx V_{IN}\times(-\Delta R_1/4R)$ because of $\Delta R_1 \ll R$. Here, a voltage $V_{OUT1}$ is used to represent the output voltage resulting from the tiny variation $\Delta R_1$. As a result, when the resistance $R_1$ has the tiny variation $\Delta R_1$, the tiny variation $\Delta R_1$ is converted into the voltage $V_{OUT}$. An amplifier (not shown) is further used to amplify the voltage $V_{OUT}$ so that a variation of the voltage $V_{OUT}$ may be measured.

Similarly, when only the resistance R2 has a tiny variation $\Delta R2$, the voltage $V_{OUT}$ satisfies $V_{OUT}=V_{IN}\times[(R/2R)-(R/(\Delta R_2+R+R))]\approx V_{IN}\times(\Delta R_2/4R)$. Here, a voltage $V_{OUT2}$ is used to represent the output voltage resulting from the tiny variation $\Delta R_2$. Preferably, the sensing resistance R-sensor is the same to the resistance $R_1$ and the reference resistance R-ref is the same to the resistance $R_2$. In theory, if the reference microcantilever 201 and the sensing microcantilever 202 have the same structure and the same material, when the environmental temperature varies and the tiny variations $\Delta R_1$ and $\Delta R_2$ satisfy $\Delta R_1=\Delta R_2$, the voltages $V_{OUT1}$ and $V_{OUT2}$ can neutralize each other.

In one practical application, the material deposited on the sensing microcantilever 202 is different from that deposited on the reference microcantilever 201 due to different measuring functions. Therefore, when the environmental temperature varies and the tiny variations $\Delta R_1$ and $\Delta R_2$ satisfy $\Delta R_1 \neq \Delta R_2$, the bimorph effect of the reference microcantilever 201 and that of the sensing microcantilever 202 can affect the detection precision. Besides, if the acid-base concentration, such as the pH value, of the analyte solution varies, it is possible to result in the condition that the voltage $V_{OUT1}$ is out of phase with the voltage $V_{OUT2}$, which interferes the interpretation of the produced real signal.

Please refer to FIG. 2(b), which is a schematic diagram showing voltages obtained from the conventional microcantilevers with pH values of an analyte solution. In FIG. 2(b), the time when an analyte solution reacts with the sensing microcantilever 202 and the time when the analyte solution reacts with the reference microcantilever 201 are expressed in the abscissa axis, and the unit in the abscissa axis is the minute. The unit in the ordinate axis is the volt. The hollow circles denote the voltage points obtained by measuring with the sensing microcantilever 202. The solid circles denote the voltage points obtained by measuring with the reference microcantilever 201. It can be seen in FIG. 2(b) that the pH value of the analyte solution is gradually changed from a smaller value to a larger value with time. When the time reaches the time point of 260 minutes, the pH value of the analyte solution is 12 and the voltage obtained by measuring with the sensing microcantilever 202 is out of phase with the voltage obtained by measuring with the reference microcantilever 201, so that what the produced real voltages mean cannot be interpreted.

SUMMARY OF THE INVENTION

In view of the disadvantages of the prior art, the present invention provides a system and method for compensating a thermal effect of a microcantilever. The apparatus includes a buried piezoresistor having a first piezoresistance relation to a temperature variation and the microcantilever having a second piezoresistance relation to the temperature variation, and uses the first and the second piezoresistance relations to compensate the thermal effect. The system and method may eliminate the influence of both of the resistance temperature coefficient effect and the bimorph effect on the microcantilever.

It is therefore an aspect of the present invention to provide a system for compensating a thermal effect. The system includes a substrate structure and a microcantilever. The substrate structure includes a first piezoresistor. The first piezoresistor is buried in the substrate structure and has a first piezoresistance having a first relation to a first variable temperature. The microcantilever has the thermal effect and a second piezoresistance having a second relation to the first variable temperature, wherein the they effect is compensated based on the first and the second relations.

It is therefore another aspect of the present invention to provide a method for compensating a thermal effect. The method includes the following steps. A first piezoresistance of a first object is measured to estimate a temperature variation for obtaining an estimated temperature. A first estimated piezoresistance is obtained according to the estimated temperature. In addition, the thermal effect of a second object due to the temperature variation is compensated by using the first estimated piezoresistance.

It is still another aspect of the present invention to provide a thermal-effect compensating apparatus. The thermal-effect compensating apparatus includes a substrate structure and a microcantilever. The substrate structure includes a first piezoresistor buried in the substrate structure. The microcantilever is formed on the substrate structure.

BRIEF DESCRIPTION OF THE DRAWINGS

The foregoing and other features and advantages of the present invention will be more clearly understood through the following descriptions with reference to the drawings, wherein.

DETAIL DESCRIPTION OF THE PREFERRED EMBODIMENT

The present invention will now be described more specifically with reference to the following embodiments. It is to be noted that the following descriptions of preferred embodiments of this invention are presented herein for the purposes of illustration and description only; it is not intended to be exhaustive or to be limited to the precise foam disclosed.

Figure 1:
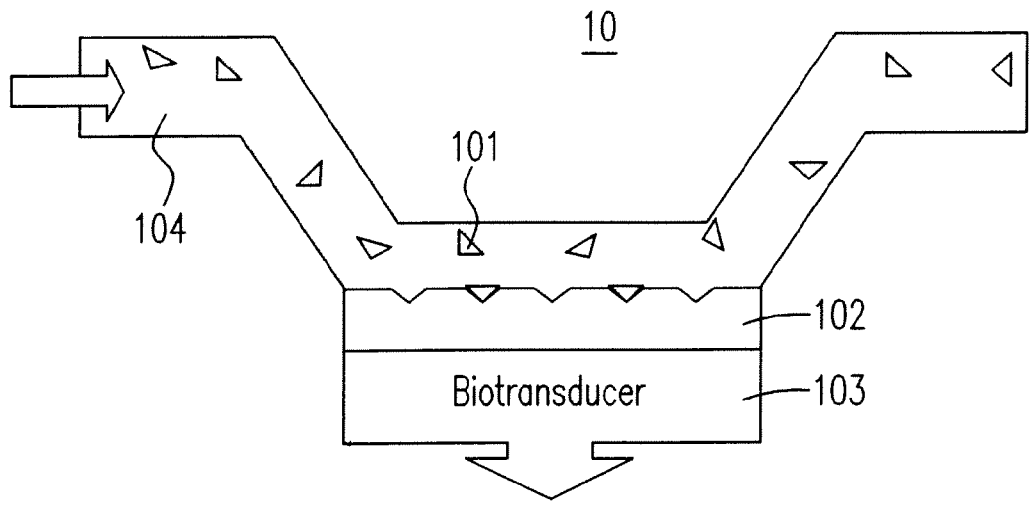
FIG. 1 is a schematic diagram showing a conventional biosensor.
Figure 2A:
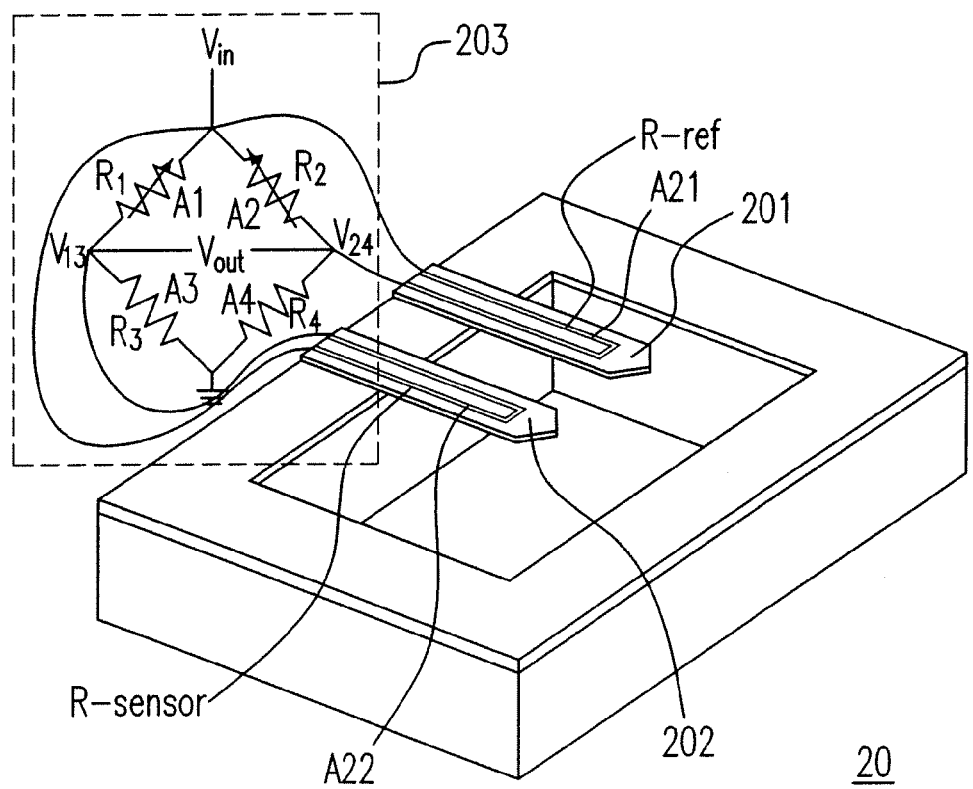
FIG. 2(a) is a schematic diagram showing a conventional microcantilever sensing apparatus.
Figure 2B:
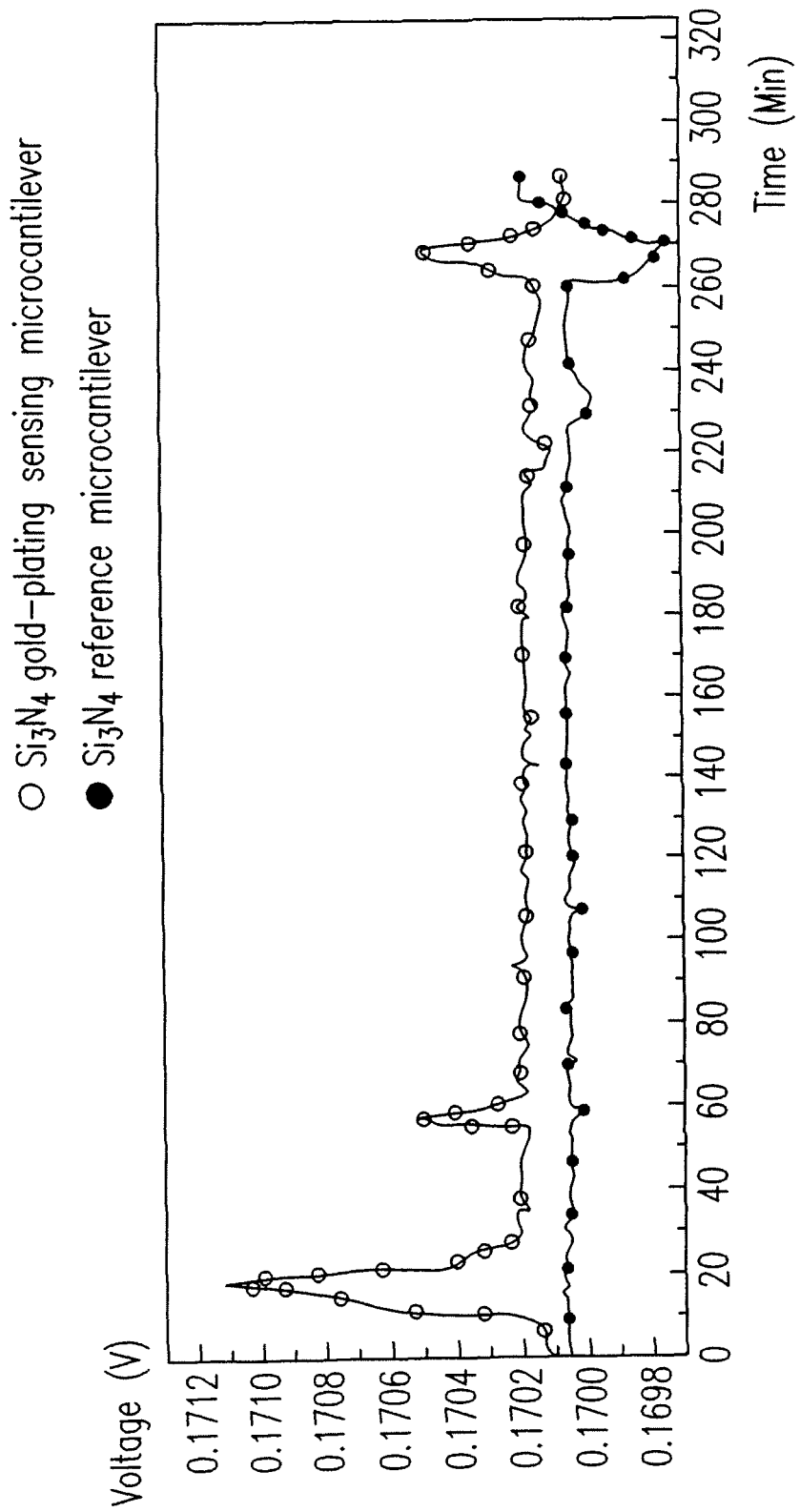
FIG. 2(b) is a schematic diagram showing voltages obtained from conventional microcantilevers with pH values of an analyte solution.
Figure 3A:
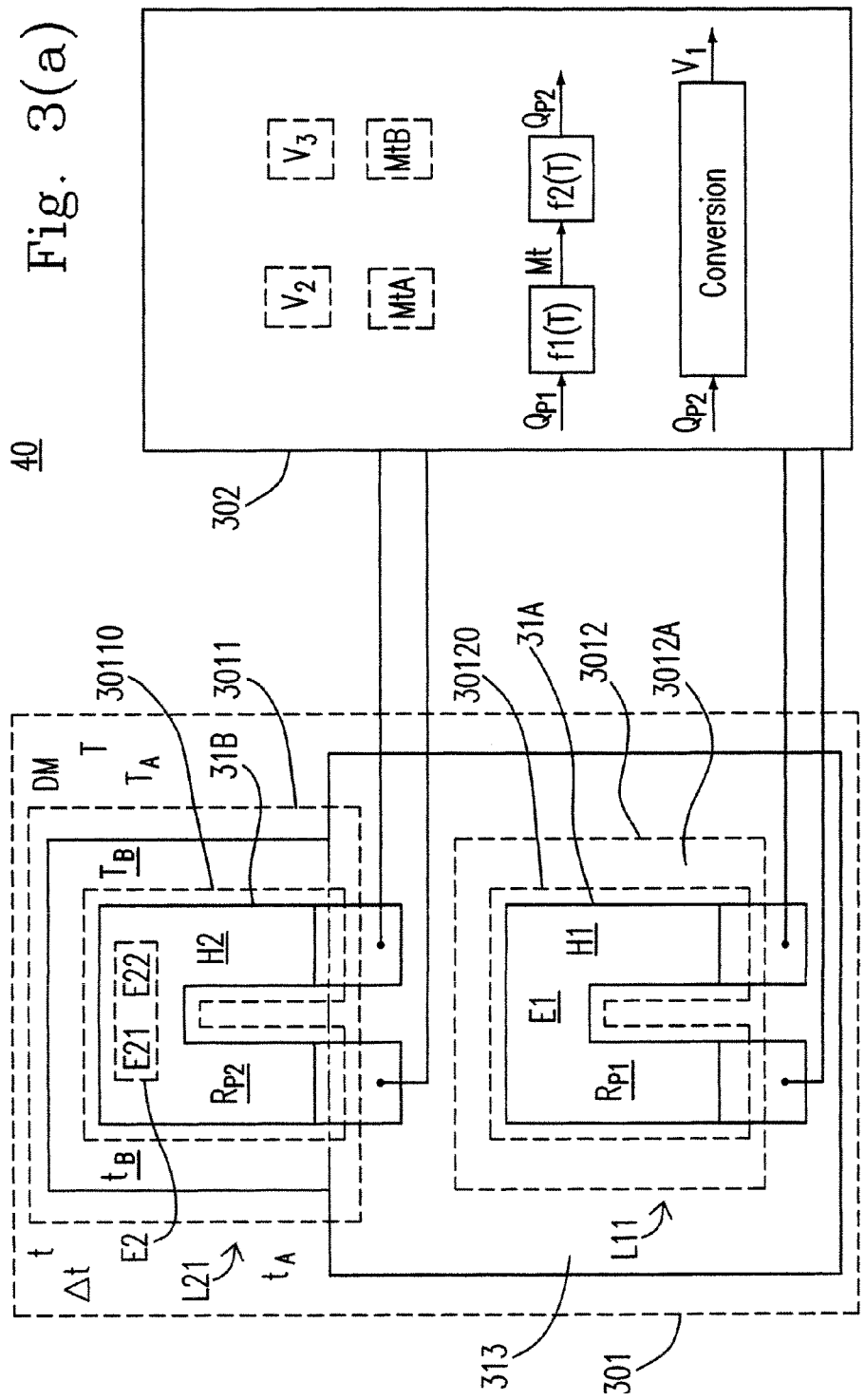
FIG. 3(a) is a schematic diagram showing a thermal-effect compensating system according to the first embodiment of the present invention.

Please refer to FIG. 3(a), which is a schematic diagram showing a thermal-effect compensating system 40 according to the first embodiment of the present invention. One preferable embodiment based on the illustration of FIG. 3(a) is described as follows. The thermal-effect compensating system 40 includes a thermal-effect compensating apparatus 301 and a processing unit 302 coupled to the thermal-effect compensating apparatus 301. In one embodiment, the thermal-effect compensating apparatus 301 includes a substrate structure 313 and a microcantilever 3011 formed on the substrate structure 313. For instance, the microcantilever 3011 is configured to stick out from the substrate structure 313. The substrate structure 313 includes a first piezoresistor 30120 buried in the substrate structure 313.

In one embodiment, the thermal-effect compensating apparatus 301 is a thermal-effect self-compensating apparatus. The substrate structure 313 includes a reference structure 3012 integrated into the substrate structure 313. The reference structure 3012 includes the first piezoresistor 30120 having a piezoresistance $R_{P1}$ and a resistance temperature coefficient effect E11, wherein the piezoresistance $R_{P1}$ is only affected by the resistance temperature coefficient effect E11. Preferably, the reference structure 3012 serves as a thermometer 3012A.

In one embodiment, the microcantilever 3011 has a sensing piezoresistor 30110 and a bimorph effect E22. The sensing piezoresistor 30110 has a piezoresistance $R_{P2}$ and a resistance temperature coefficient effect E21, wherein the piezoresistance $R_{P2}$ is affected by the resistance temperature coefficient effect E21 and the bimorph effect E22. In one embodiment, the microcantilever 3011 has a thermal effect E2, the thermal effect E2 includes the resistance temperature coefficient effect E21 and the bimorph effect E22, and the thermal-effect compensating apparatus 301 is used to compensate the thermal effect E2.

One preferable embodiment based on the illustration of FIG. 3(a) is described as follows. When a variable temperature t of the thermal-effect compensating system 40 varies, the thermal effect E2 may be produced. The thermal-effect compensating apparatus 301 of the thermal-effect compensating system 40 has the thermal effect E2, the piezoresistance $R_{P1}$ and the piezoresistance $R_{P2}$. The thermal-effect compensating system 40 compensates the thermal effect E2 by using the processing unit 302 to measure the piezoresistance $R_{P1}$ and the piezoresistance $R_{P2}$.

In one embodiment, the thermal-effect compensating apparatus 301 may include a first object 31A and a second object 31B, and have a temperature variation Δt, wherein the first object 31A and the second object 31B respectively have the piezoresistance $R_{P1}$ and the piezoresistance $R_{P2}$. The second object 31B have the thermal effect E2 resulting from the temperature variation Δt. The processing unit 302 of the thermal-effect compensating system 40 measures the piezoresistance $R_{P1}$ of the first object 31A to estimate the temperature variation Δt for obtaining an estimated temperature Mt. The processing unit 302 obtains an estimated piezoresistance $Q_{P2}$ according to the estimated temperature Mt. The thermal-effect compensating system 40 compensates the thermal effect E2 of the second object 31B due to the temperature variation Δt by using the estimated piezoresistance $Q_{P2}$.

In one embodiment, the substrate structure 313 includes the first object 31A being the first piezoresistor 30120, and the first piezoresistor 30120 is buried in the substrate structure 313 and has the piezoresistance The second object 31B is the microcantilever 3011 having the piezoresistance $R_{P2}$ and the thermal effect E2, wherein the second object 31B sticks out from the substrate structure 313. The first piezoresistor 30120 and the microcantilever 3011 are coupled to the processing unit 44 302. The processing unit measures the piezoresistances $R_{P1}$ and $R_{P2}$ according to a variable temperature T to respectively determine a temperature piezoresistance function f1(T) and a temperature piezoresistance function f2(T), both of which are associated with the variable temperature T.

In one embodiment, the temperature variation Δt is present in reference to a variable temperature t. The variable temperatures T and t are respectively ones selected from a first group and a second group, wherein the first group consists of a first environmental temperature TA and a second environmental temperature tA of the microcantilever 3011, and the second group consists of a first body temperature TB and a second body temperature tB of the microcantilever 3011. The estimated temperature Mt is an estimated environmental temperature MtA when the first group is selected, and is an estimated body temperature MtB when the second group is selected. The variable temperatures T and t may have a same temperature domain DM.

In one embodiment, the temperature piezoresistance functions f1(T) and f2(T) are determined when the first piezoresistor 30120 and the microcantilever 3011 are operated in a calibration state. When the first piezoresistor 30120 and the microcantilever 3011 are operated in a sensing state, the estimated temperature Mt, the estimated piezoresistance $Q_{P2}$ are obtained and the thermal effect E2 is compensated. In order to obtain the estimated temperature Mt, the piezoresistance $R_{P1}$ is measured at the temperature variation Δt to obtain an estimated piezoresistance $Q_{P1}$. The estimated temperature Mt is obtained according to the estimated piezoresistance $Q_{P1}$ and the temperature piezoresistance function f1(T). The estimated piezoresistance $Q_{P2}$ may be obtained according to the estimated temperature Mt1 and the temperature piezoresistance function f2(T).

In one embodiment, the processing unit 302 converts the estimated piezoresistance $Q_{P2}$ into a signal $V_1$, and measures the piezoresistance $R_{P2}$ at the temperature variation At to produce a signal $V_2$. The processing unit 302 compensates the signal $V_2$ for the temperature variation Δt by using the signal $V_1$, thereby the thermal-effect compensating system 40 compensates the piezoresistance $R_{P2}$ for the thermal effect E2.

One preferable embodiment based on the illustration of FIG. 3(a) is described as follows. The thermal-effect compensating system 40 includes the thermal-effect compensating apparatus 301 and the processing unit 302. For instance, the thermal-effect compensating system 40 includes the substrate structure 313 and the microcantilever 3011. The substrate structure 313 includes the first piezoresistor 30120. The piezoresistor is buried in the substrate structure 313 and has the piezoresistance $R_{P1}$ having a relation H1 to the variable temperature T. The microcantilever 3011 has the thermal effect E2 and the piezoresistance $R_{P2}$ having a relation H2 to the variable temperature T, wherein the thermal effect E2 is compensated based on the relations H1 and H2.

In one embodiment, the processing unit 302 is coupled to the first piezoresistor 30120 and the microcantilever 3011, and measures the piezoresistance $R_{P1}$ at the temperature variation Δt to obtain the estimated piezoresistance $Q_{P1}$. The thermal-effect compensating system 40 uses the estimated piezoresistance $Q_{P1}$ and the relations Hl and H2 to compensate the second piezoresistance $R_{P2}$ for the thermal effect E2.

In one embodiment, the temperature variation Δt is present in reference to the variable temperature t. The variable temperatures T and t are respectively ones selected from the first group and the second group, wherein the first group consists of the first environmental temperature $T_A$ and the second environmental temperature $t_A$ of the microcantilever 3011, and the second group consists of the first body temperature $T_B$ and the second body temperature $t_B$ of the microcantilever 3011. The variable temperature T has the temperature domain DM, and the variable temperature t varies in the temperature domain DM. The thermal-effect compensating system 40 is a thermal-effect self-compensating system. The thermal-effect compensating system 40 uses the processing unit 302 to characterize the relations H1 and H2. The relation H1 is characterized as the temperature piezoresistance function f1(T) of the variable temperature T, e.g. a first quadratic equation. The relation H2 is characterized as the temperature piezoresistance function f2(T) of the variable temperature T, e.g. a second quadratic equation.

In one embodiment, the processing unit 302 estimates the temperature variation Δt according to the estimated piezoresistance $Q_{P1}$ and the temperature piezoresistance function f1(T) to obtain the estimated temperature Mt, wherein the estimated temperature Mt is the estimated environmental temperature MtA when the first group is selected, and is the estimated body temperature MtB when the second group is selected. The processing unit 302 obtains the estimated piezoresistance $Q_{P2}$ according to the estimated temperature Mt and the temperature piezoresistance function f2(T), and converts the estimated piezoresistance $Q_{P2}$ into the signal $V_1$. The processing unit 302 measures the second piezoresistance $R_{P2}$ at the temperature variation Δt to produce the signal $V_2$, and uses the signal $V_1$ to compensate the signal $V_2$ for the temperature variation Δt, thereby the thermal-effect compensating system 40 compensates the piezoresistance $R_{P2}$ for the thermal effect E2. The first piezoresistor 30120 further has the resistance temperature coefficient effect E11, and the temperature piezoresistance function f1(T) is only associated with the resistance temperature coefficient effect E11. The thermal effect E2 of the microcantilever 3011 has the resistance temperature coefficient effect E21 and the bimorph effect E22, and the temperature piezoresistance function f2(T) is associated with the resistance temperature coefficient E21 and the bimorph effects E22.

In one embodiment, the substrate structure 313 includes the reference structure 3012 integrated into the substrate structure 313. The reference structure 3012 includes the first piezoresistor 30120 further having the resistance temperature coefficient effect E11, and the piezoresistance $R_{P1}$ is only affected by the resistance temperature coefficient effect E11. The reference structure 3012 serves as a thermometer 3012A, and the thermometer 3012A is used to measure the variable temperatures T and t and the temperature variation Lt. The microcantilever 3011 has the bimorph effect E22 and the sensing piezoresistor 30110 coupled to the processing unit 302. The sensing piezoresistor 30110 has the piezoresistance $R_{P2}$ and the resistance temperature coefficient effect E21, wherein the piezoresistance $R_{P2}$ is affected by the resistance temperature coefficient effect E21 and the bimorph effect E22.

In one embodiment, the microcantilever 3011 is structured by referring to the reference structure 3012, and each of the first piezoresistor 30120 and the sensing piezoresistor 30110 is made of a first material having a piezoresistive property, wherein the first material includes a semiconductor material being one of a polycrystalline silicon and a monocrystalline silicon. The reference structure 3012 and the microcantilever 3011 are respectively made of a first multilayer composite material and a second multilayer composite material. The first and the second multilayer composite materials respectively include layers L11 and L12 made of a semiconductor material being one of a polycrystalline silicon and a monocrystalline silicon.

Figure 3B:
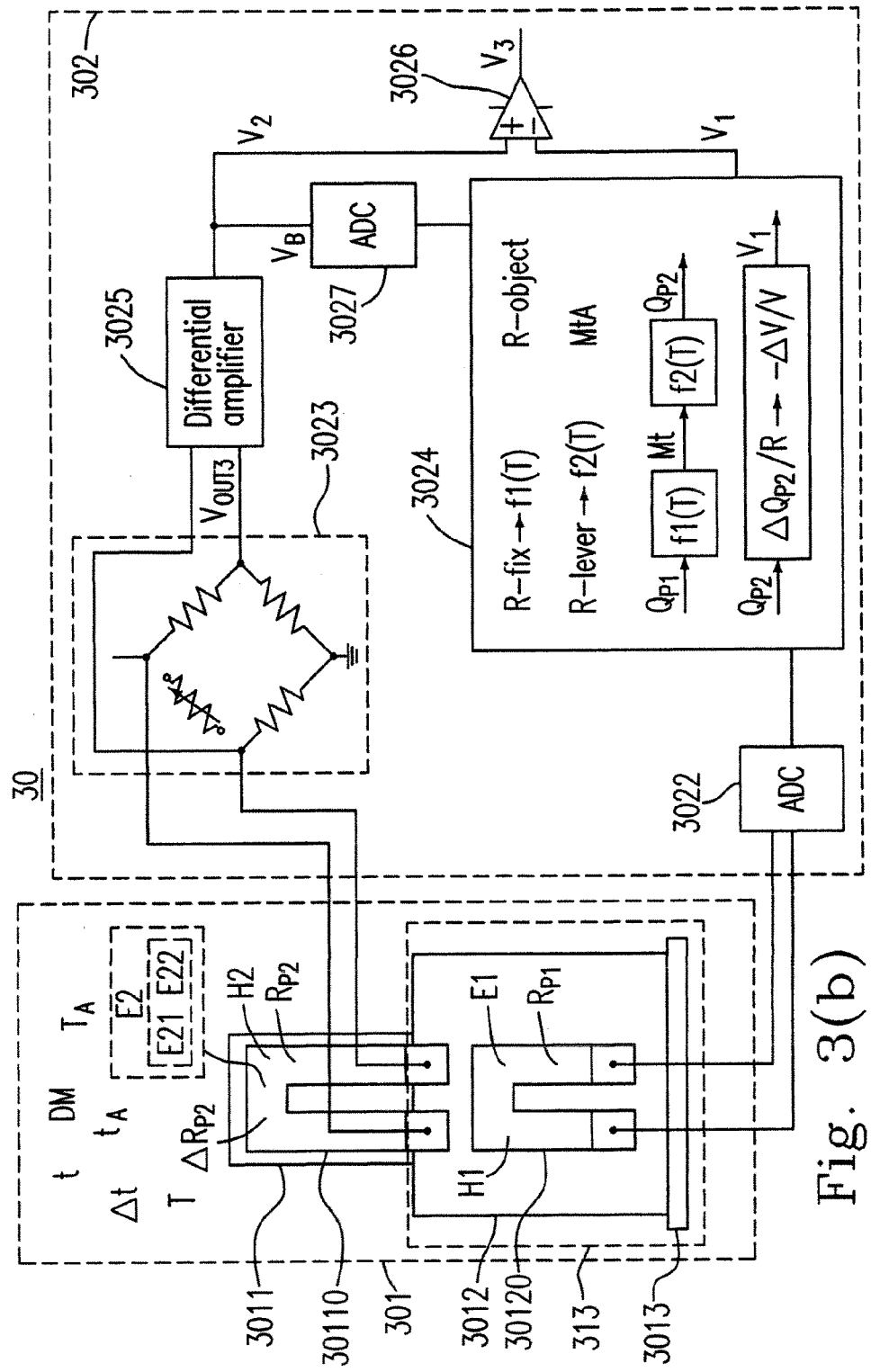
FIG. 3(b) is a schematic diagram showing a thermal-effect compensating system according to the second embodiment of the present invention.

Please refer to FIG. 3(b), which is a schematic diagram showing a thermal-effect compensating system 30 according to the second embodiment of the present invention. The thermal-effect compensating system 30 includes a thermal-effect compensating apparatus 301 and a processing unit 302 coupled to the thermal-effect compensating apparatus 301. The thermal-effect compensating apparatus 301 may be a thermal-effect self-compensating apparatus and be a piezoresistive sensor. The thermal-effect compensating apparatus 301 includes the substrate structure 3013 and the microcantilever 3011 sticking out from the substrate structure 3013. The microcantilever 3011 may be a piezoresistive transducer. The substrate structure 3013 includes a substrate 3013 and the reference structure 3012 formed on the substrate 3013, wherein the reference structure 3012 is integrated into the substrate structure 3013.

The reference structure 3012 includes the first piezoresistor 30120 buried in the substrate structure 3013. The first piezoresistor 30120 may be a reference piezoresistor and has the piezoresistance $R_{P1}$. The microcantilever 3011 is structured by referring to the reference structure 3012. The microcantilever 3011 includes the sensing piezoresistor 30110 having the piezoresistance $R_{P2}$. The processing unit 302 includes an analog-digital converter 3022, a Wheatstone bridge 3023, a computer 3024, a differential amplifier 3025, a subtracter 3026 and an analog-digital converter 3027. The first piezoresistor 30120 and the sensing piezoresistor 30110 are coupled to the processing unit 302. The analog-digital converter 3022 is coupled between the first piezoresistor 30120 and the computer 3024; the Wheatstone bridge 3023 is coupled to the sensing piezoresistor 30110; the differential amplifier 3025 is coupled to the Wheatstone bridge 3023; the analog-digital converter 3027 is coupled between the differential amplifier 3025 and the computer 3024.

The microcantilever 3011 has the thermal effect E2 due to a temperature variation of the microcantilever 3011. The thermal-effect compensating system 30 is used to self-compensate the thermal effect E2 and has a calibration state and a sensing state. When in the calibration state, the thermal effect E2 is affected by the variable temperature T of the microcantilever 3011; for example, the variable temperature T is the environmental temperature $T_A$ of the microcantilever 3011 and has the temperature domain DM. When in the sensing state, the thermal effect E2 is affected by the variable temperature t of the microcantilever 3011; for example, the variable temperature t is the environmental temperature $t_A$ of the microcantilever 3011, has the temperature variation Δt, and varies in the temperature domain DM.

In one embodiment, when in the calibration state, the analyte is not applied to the microcantilever 3011 and operations are performed as follows: the computer 3024 uses the analog-digital converter 3022 to measure the piezoresistance $R_{P1}$ for obtaining an estimated piezoresistance R-fix associated with the variable temperature T. The Wheatstone bridge 3023 produces a voltage $V_{OUT3}$ in response to the piezoresistance $R_{P2}$ affected by the variable temperature T. The differential amplifier 3025 produces the signal $V_B$ in response to the voltage $V_{OUT3}$. The computer 3024 uses the analog-digital converter 3027 to convert the signal $V_B$ for obtaining an estimated piezoresistance R-lever associated with the variable temperature T. The computer 3024 expresses the estimated piezoresistance R-fix as the temperature piezoresistance function f1(T) and expresses the estimated piezoresistance R-lever as the temperature piezoresistance function f2(T). That is to say, the piezoresistances $R_{P1}$ and $R_{P2}$ are respectively estimated at the temperature piezoresistance functions f1(T) and f2(T) of the variable temperature T.

In one embodiment, the thermal-effect compensating apparatus 301 is put into a temperature control apparatus (not shown) in a laboratory beforehand. Then, the calibration state starts, the computer 3024 controls the operations in the calibration state by a program, and the temperature control apparatus gradually heats the thermal-effect compensating apparatus 301 to vary the variable temperature T for obtaining the temperature piezoresistance functions f1(T) and f2(T).

In one preferable embodiment, when in the sensing state, operations are performed as follows. The sensing piezoresistor 30110 is coupled to the Wheatstone bridge 3023 and is measured thereby. The Wheatstone bridge 3023 produces the voltage $V_{OUT3}$ in response to a tiny variation of the piezoresistance $R_{P2}$. The differential amplifier 3025 receives the voltage $V_{OUT3}$ and amplifies the voltage $V_{OUT3}$ to produce the signal $V_2$, wherein the voltage $V_{OUT3}$ is proportional to a piezoresistance variation $\Delta R_{P2}$ of the piezoresistance $R_{P2}$ operating in the condition that the analyte may be applied to the microcantilever 3011. The computer 3024 uses the analog-digital converter 3022 to measure the piezoresistance $R_{P1}$ at the temperature variation $\Delta t$ for obtaining the estimated piezoresistance $Q_{P1}$. The computer 3024 transforms the estimated piezoresistance $Q_{P1}$ into the estimated temperature Mt according to the temperature piezoresistance function f1(T), and substitutes the estimated temperature Mt into the temperature piezoresistance function f2(T) to obtain the estimated piezoresistance $Q_{P2}$. The thermal-effect compensating system 30 uses the estimated piezoresistance $Q_{P2}$ to compensate the piezoresistance $R_{P2}$ for the thermal effect E2, wherein the estimated piezoresistance $Q_{P2}$ represents the piezoresistance $R_{P2}$ operating in the condition that the analyte is not applied to the microcantilever 3011.

The calibration state of the thermal-effect compensating system 30 is further described as follows. The estimated piezoresistances R-fix and R-lever are affected by the variable temperature T, such as the environmental temperature $T_A$; that is, each of the estimated piezoresistances R-fix and R-lever is a function of the variable temperature T. Therefore, the estimated piezoresistance R-fix may be expressed as a temperature piezoresistance function $f1(T)=aT^2+bT+c$, and the estimated piezoresistance R-lever may be expressed as a temperature piezoresistance function $f2(T)=dT^2+eT+f$, wherein T denotes the variable temperature, a, b, c, d, e and f denote material coefficients, and the temperature piezoresistance functions f1(T) and f2(T) are applied to the temperature domain DM of the variable temperature T. When in the heating process, the estimated piezoresistances R-fix and R-lever are recorded with increase in the variable temperature T. According to this method, two curves can be plotted in the diagram, each curve shows the relation between the piezoresistance and the variable temperature T, and the material coefficients a, b, c, d, e and f may be found out. In the present invention, the reference numeral t denotes the variable temperature in the sensing state in order to be distinguished from the variable temperature T in the calibration state.

Figure 4A:
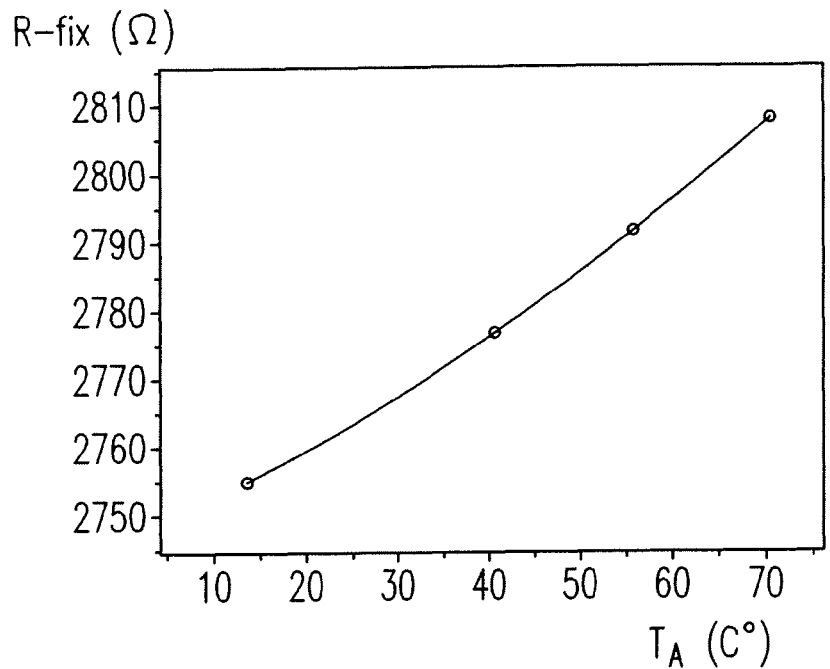
FIG. 4(a) and FIG. 4(b) are schematic diagrams showing estimated piezoresistances varying with an environmental temperature according to the second embodiment of the present invention.

Please refer to FIG. 4(a), which is a schematic diagram showing the estimated piezoresistance R-fix varying with the environmental temperature $T_A$ according to the second embodiment of the present invention. The environmental temperature $T_A$ is expressed in the abscissa axis. The estimated piezoresistance R-fix is expressed in the ordinate axis. In view of FIG. 4(a), when the environmental temperature $T_A$ increases, the estimated piezoresistance R-fix also increases therewith. The estimated piezoresistance R-fix has a value being about 2775Ω at the environmental temperature 41° C.

Figure 4B:
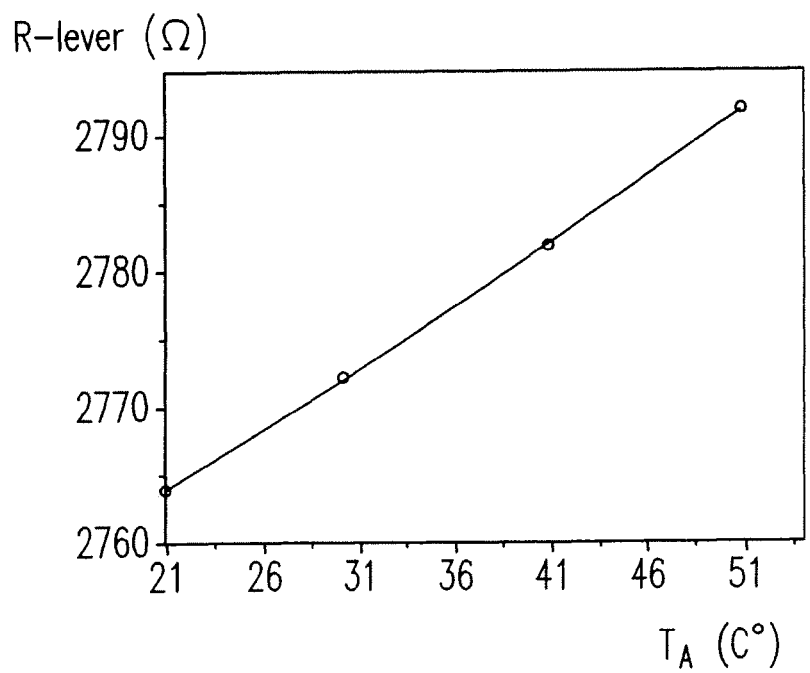

Please refer to FIG. 4(b), which is a schematic diagram showing the estimated piezoresistance R-lever varying with the environmental temperature $T_A$ according to the second embodiment of the present invention. The environmental temperature $T_A$ is expressed in the abscissa axis. The estimated piezoresistance R-lever is expressed in the ordinate axis. In view of FIG. 4(b), when the environmental temperature $T_A$ increases, the estimated piezoresistance R-lever also increases therewith. The estimated piezoresistance R-lever has a value being about 2782Ω at the environmental temperature 41° C.

The first piezoresistor 30120 is buried in the substrate structure 3013 and has the resistance temperature coefficient effect E11 associated with the variable environmental temperature $T_A$. Compared with the resistance temperature coefficient effect E11 of the reference structure 3012, the bimorph effect of the reference structure 3012 is negligible. Because the estimated piezoresistance R-fix does not belong to the microcantilever 3011 but does belong to the first piezoresistor 30120, the estimated piezoresistance R-fix can only be affected by the resistance temperature coefficient effect E11 of the first piezoresistor 30120 and cannot be affected by the bimorph effect of the reference structure 3012. The microcantilever 3011 has the thermal effect E2 associated with the variable environmental temperature $T_A$. The thermal effect E2 includes the resistance temperature coefficient effect E21 and the bimorph effect E22, each of which cannot be neglected. Because the estimated piezoresistance R-lever belongs to the microcantilever 3011, the estimated piezoresistance R-lever is affected by both of the resistance temperature coefficient effect E21 and the bimorph effect E22. This results in that the estimated piezoresistances R-fix and R-lever have different estimated piezoresistance values at the same environmental temperature.

The sensing state of the thermal-effect compensating system 30 is further described as follows. When in the sensing state, the Wheatstone bridge 3023 measures the sensing piezoresistor 30110 to produce the voltage $V_{OUT3}$ in response to the tiny variation of the second piezoresistance $R_{P2}$, wherein the voltage $V_{OUT3}$ is proportional to the variation of the piezoresistance $R_{P2}$ operating in the condition that the analyte may be applied to the microcantilever 3011, and the differential amplifier 3025 produce the signal $V_2$ in response to the voltage $V_{OUT3}$. In order that the thermal-effect compensating system 30 uses the piezoresistance $R_{P1}$ of the reference structure 3012 to compensate the piezoresistance $R_{P2}$ of the microcantilever 3011 for the temperature variation $\Delta t$ of the variable temperature t, preferable operations in the sensing state may be performed as follows. The computer 3024 uses the analog-digital converter 3022 to measure the piezoresistance $R_{P1}$ at the temperature variation $\Delta t$ for obtaining the estimated piezoresistance $Q_{P1}$. The computer 3024 substitutes the estimated piezoresistance $Q_{P1}$ into the temperature piezoresistance function $f1(T)=aT^2+bT+c$ to find out the estimated temperature Mt, such as the estimated environmental temperature MtA. The computer 3024 substitutes the estimated temperature Mt into the temperature piezoresistance function $f2(T)=dT^2+eT+f$ to find out the estimated piezoresistance $Q_{P2}$. The estimated piezoresistance $Q_{P2}$ represents the piezoresistance $R_{P2}$ operating in the condition that the microcantilever 3011 is purely affected by both of the resistance temperature coefficient effect E21 and the bimorph effect E22 resulting from the variable temperature t and is not affected by the stress resulting from the analyte loaded upon the microcantilever 3011. The reference piezoresistor 30120 may serve as a thermometer 3012A used to measure the variable temperatures T and t and the temperature variation Δt.

Under the condition the microcantilever 3011 loads with the analyte in the sensing state and the variable temperatures t has the temperature variation Δt, the sensing piezoresistor 30110 has the piezoresistance $R_{P2}$ and the piezoresistance $R_{P2}$ has a piezoresistance variation $\Delta R_{P2}$. Using the analog-digital converter 3027 in response to the signal $V_2$, the computer 3024 may estimate the piezoresistance $R_{P2}$ to obtain an estimated piezoresistance R-object. The estimated piezoresistance R-object is not only affected by both of the resistance temperature coefficient effect E21 and the bimorph effect E22 but also affected by the stress resulting from the analyte loaded upon the microcantilever 3011. Therefore, the processing unit 302 may makes the process that the estimated piezoresistance $Q_{P2}$ is subtracted from the estimated piezoresistance R-object. Through the process, the influence of both of the resistance temperature coefficient effect E21 and the bimorph effect E22 on the microcantilever 3011 may be neutralized and an estimated piezoresistance of the microcantilever 3011 without the influence in the variable temperature t may be obtained. That is to say, the piezoresistance $R_{P1}$ has the relation H1 to the variable temperature T, the piezoresistance $R_{P2}$ has the relation H2 to the variable temperature T, and the thermal-effect compensating system 30 may compensate the thermal effect E2 of the microcantilever 3011 according to the relations H1 and H2 when the variable temperature t varies.

In FIG. 3(b), when the variable temperature t varies in the sensing state, the piezoresistance $R_{P2}$ also varies therewith. When the piezoresistance $R_{P2}$ varies, the Wheatstone bridge 3023 converts the piezoresistance variation $\Delta R_{P2}$ of the piezoresistance $R_{P2}$ into the voltage $V_{OUT3}$, the differential amplifier 3025 amplifies the voltage $V_{OUT3}$ to output the signal $V_2$. When the variable temperature t varies, the estimated piezoresistance $Q_{P2}$ also varies therewith. When the estimated piezoresistance $Q_{P1}$ varies, the computer 3024 obtains the estimated piezoresistance $Q_{P2}$ according to the estimated piezoresistance $Q_{P1}$, the temperature piezoresistance function f1(T) and the temperature piezoresistance function f2(T). The computer 3024 emulates the Wheatstone bridge 3023 and the amplifier 3025 to convert the estimated piezoresistance $Q_{P2}$ into the signal $V_1$, wherein emulating the Wheatstone bridge 3023 and the amplifier 3025 is denoted in FIG. 3(b) by the reference numerals $\Delta Q_{P2}/R \rightarrow -\Delta V/V$. The subtracter 3026 receives the signals $V_1$ and $V_2$ and subtracts the signal $V_1$ from the signal $V_2$ to output the signal $V_3$ unaffected by the variable temperature t, wherein the signal $V_3$ is provided without both of the resistance temperature coefficient effect E21 and the bimorph effect E22. That is to say, when the variable temperature t varies, the thermal-effect compensating system 30 uses the signal $V_1$ to compensate the signal $V_2$ for the temperature variation Δt, thereby compensates the piezoresistance $R_{P2}$ for the thermal effect E2.

Figure 5A:
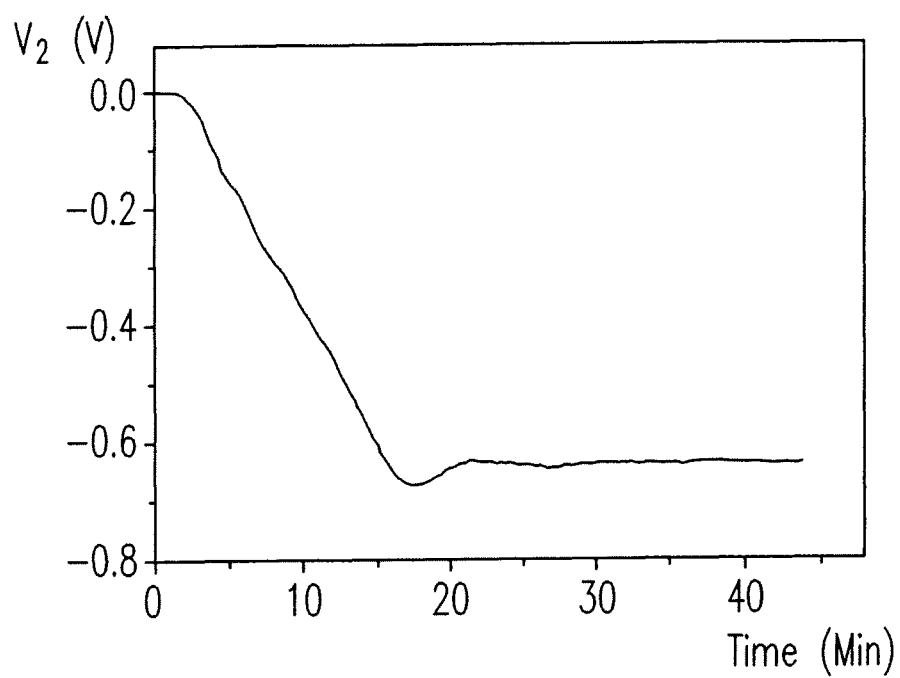
FIG. 5(a), FIG. 5(b) and FIG. 5(c) are schematic diagrams showing signals varying with time according to the second embodiment of the present invention.

Please refer to FIG. 5(a), which is a schematic diagram showing the signal $V_2$ varying with time according to the second embodiment of the present invention. The time is expressed in the abscissa axis and represents the environmental temperature $t_A$ proportional to the time. The signal $V_2$ is expressed in the ordinate axis. For instance, when the environmental temperature $t_A$ increases from 13.6° C. to 40.7° C. with increase in time, the signal $V_2$ varies from 0V to about −0.64V and has a voltage variation of about −23.6 μV per 1° C. The voltage variation results from both of the resistance temperature coefficient effect E21 and the bimorph effect E22.

Figure 5B:
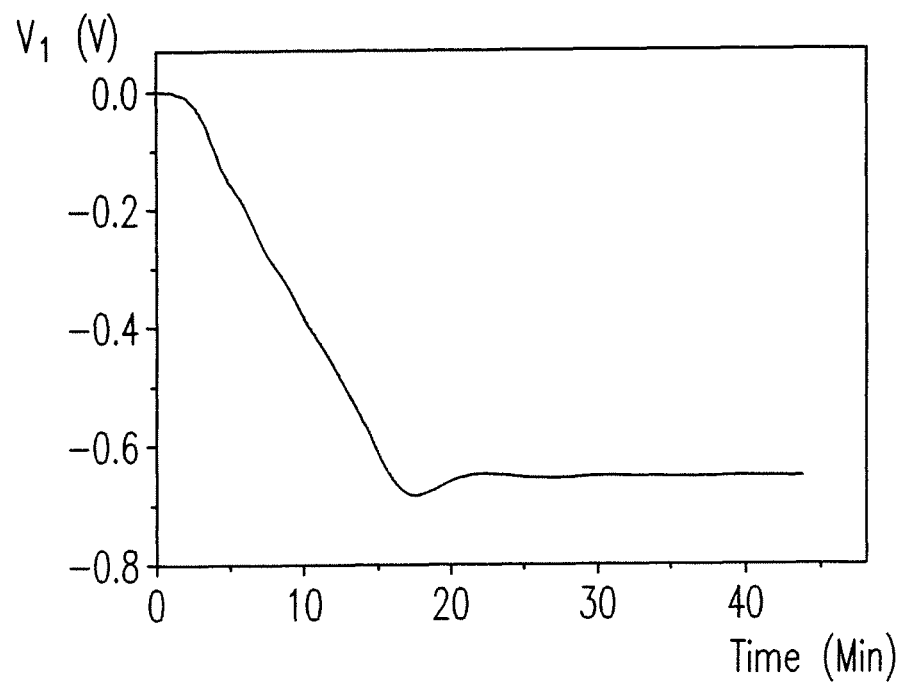

Please refer to FIG. 5(b), which is a schematic diagram showing the signal $V_1$ varying with the time according to the second embodiment of the present invention. The time is expressed in the abscissa axis and represents the environmental temperature $t_A$ proportional to the time. The signal $V_1$ is expressed in the ordinate axis.

Figure 5C:
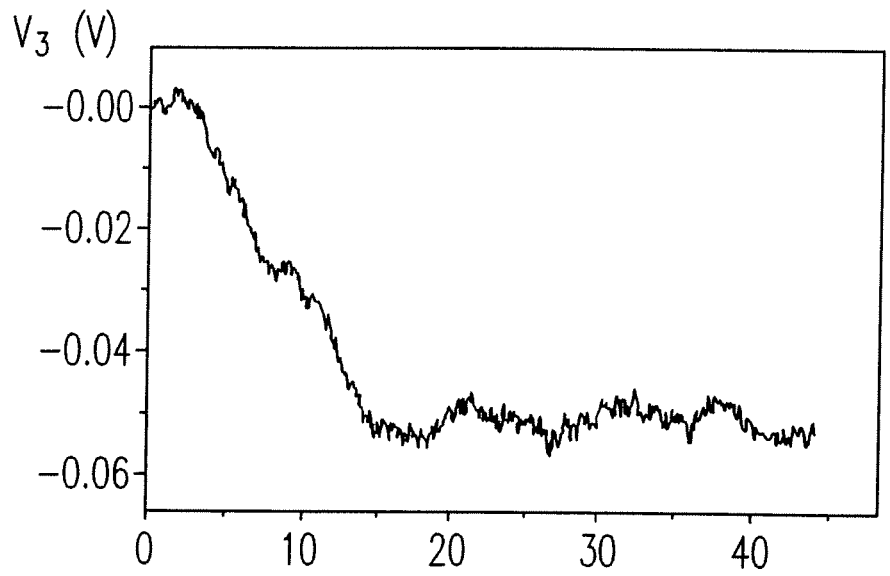

Please refer to FIG. 5(c), which is a schematic diagram showing the signal $V_3$ varying with the time according to the second embodiment of the present invention. The time is expressed in the abscissa axis and represents the environmental temperature $t_A$ proportional to the time. The signal $V_3$ is expressed in the ordinate axis. The signal $V_3$ is provided without both of the resistance temperature coefficient effect E21 and the bimorph effect E22. The signal $V_3$ in FIG. 5(c) may be obtained by subtracting the signal $V_1$ from the signal $V_2$. It may be found out according to the illustration in FIG. 5(c) that: when the environmental temperature $t_A$ increases from 13.6° C. to 40.7° C. with increase in time, the signal $V_3$ varies from 0V to about −0.052V, and the signal $V_3$ has a voltage variation of about −2 μV per 1° C. when the environmental temperature $t_A$ has a value of 27.1° C. The signal $V_3$ in FIG. 5(c) is smaller than 1/10 of the signal $V_2$, which is not compensated.

Figure 6:
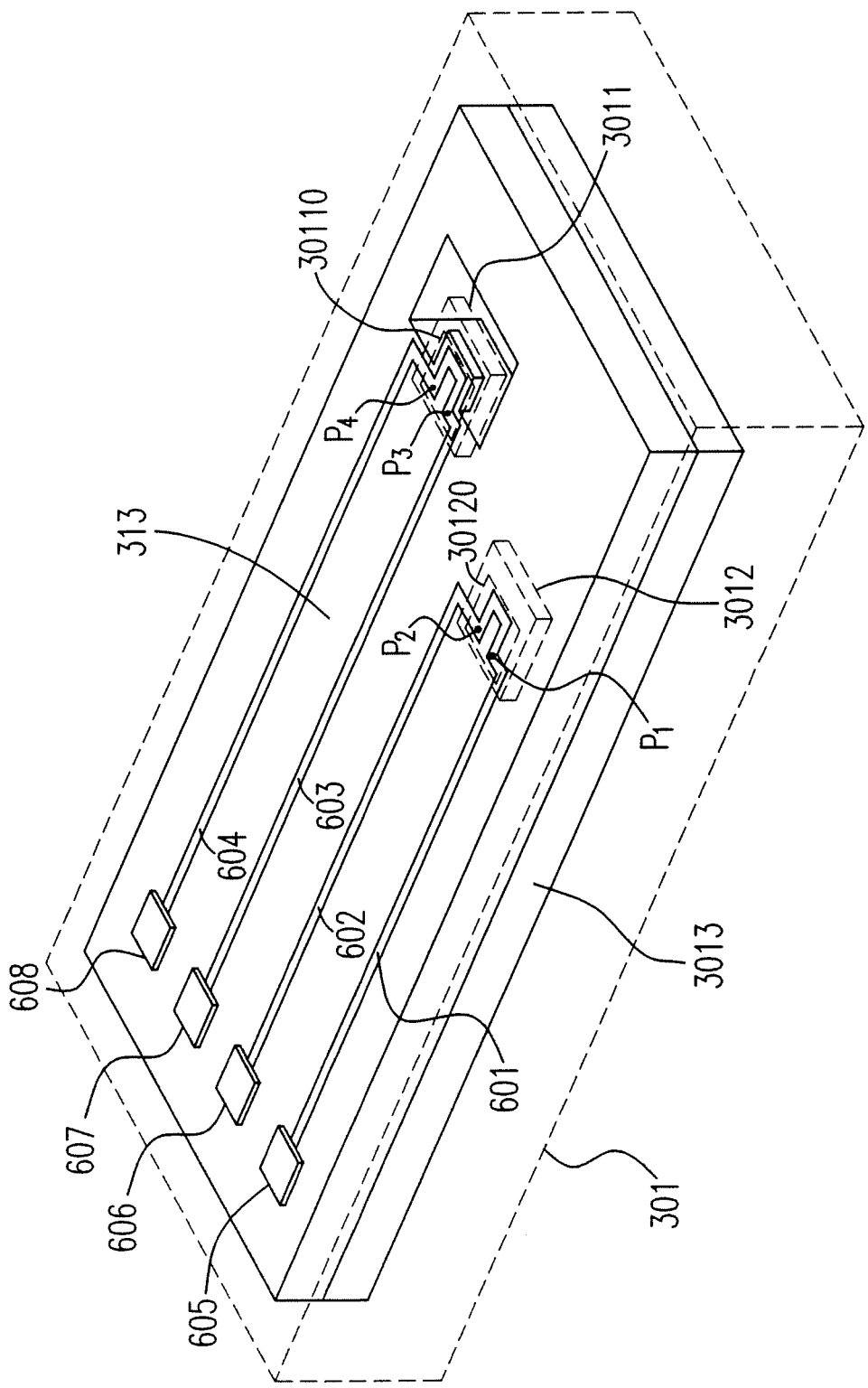
FIG. 6 is a schematic diagram showing a thermal-effect compensating apparatus according to the second embodiment of the present invention.

Please refer to FIG. 6, which is a schematic diagram showing the thermal-effect compensating apparatus 301 according to the second embodiment of the present invention. The thermal-effect compensating apparatus 301 includes the substrate structure 313 and the microcantilever 3011, and the substrate structure 313 includes the substrate 3013 and the reference structure 3012. The microcantilever 3011 includes the sensing piezoresistor 30110. The reference structure 3012 includes the first piezoresistor 30120. The first piezoresistor 30120 has a terminal P1 and a terminal P2. The terminal P1 is connected with a wire 601, and the wire 601 is connected to a conducting pad 605. The terminal P2 is connected with a wire 602, and the wire 602 is connected to a conducting pad 606.

As shown in FIG. 6, the sensing piezoresistor 30110 has a terminal P3 and a terminal P4. The terminal P3 is connected with the wire 603, and the terminal P4 is connected with the wire 604. The wire 603 is connected to a conducting pad 607, and the wire 604 is connected to a conducting pad 608. The microcantilever 3011 is structured by referring to the reference structure 3012, and each of the first piezoresistor 30120 and the sensing piezoresistor 30110 is made of a first material having a piezoresistive property, wherein the first material includes a semiconductor material being one of a polycrystalline silicon and a monocrystalline silicon.

In order to prevent leakage of electricity and satisfy equilibrium of inner stress, the microcantilever 3011 used in the present invention includes five layers of materials. The materials and the thicknesses of the microcantilever 3011 from the top layer to the bottom layer are shown in Table 2. The layer of the polycrystalline silicon of the microcantilever 3011 is used to form the sensing piezoresistor 30110 of the microcantilever 3011. The reference structure 3012 includes four layers of materials. The four materials and the four thicknesses of the reference structure 3012 may be the same as those of four lower layers of the microcantilever 3011, and the gold layer in the microcantilever 3011 may be omitted in the reference structure 3012. The layer of the polycrystalline silicon of the reference structure 3012 is used to form the first piezoresistor 30120 of the reference structure 3012.

TABLE 2

| Layer material | Thickness (nm) |
| --- | --- |
| Gold | 35 |
| Silicon nitride | 350 |
| Polycrystalline silicon | 180 |
| Silicon nitride | 600 |
| Silica | 100 |

Figure 7:
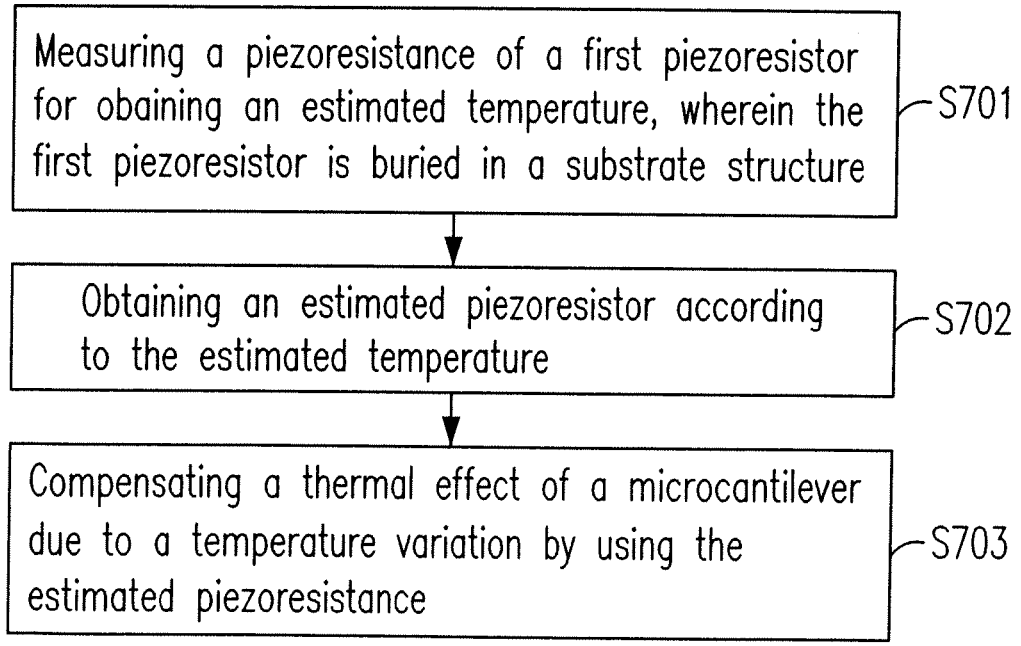
FIG. 7 is a schematic diagram showing a compensating method of the thermal-effect compensating system according to the second embodiment of the present invention.

Please refer to FIG. 7, which is a flow diagram showing a compensating method of the thermal-effect compensating system 30 according to the second embodiment of the present invention. The compensating method is described as follows:

In Step 701, the piezoresistance $R_{P1}$ of the first piezoresistor 30120 is measured for obtaining the estimated temperature Mt, wherein the first piezoresistor 30120 is buried in the substrate structure 313.

In Step 702, the estimated piezoresistance $Q_{P2}$ is obtained according to the estimated temperature Mt.

In Step 703, the thermal effect E2 of the microcantilever 3011 due to the temperature variation Δt is compensated by using the estimated piezoresistance $Q_{P2}$.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims, which are to be accorded with the broadest interpretation so as to encompass all such modifications and similar structures.

What is claimed is:

1. A system for compensating a thermal effect, comprising:
a substrate structure comprising:
a first piezoresistor buried in the substrate structure and having a first piezoresistance having a first relation to a first variable temperature; and
a microcantilever having the thermal effect and a second piezoresistance having a second relation to the first variable temperature, wherein the thermal effect is compensated based on the first and the second relations.

2. A system according to claim 1, measuring the first piezoresistance at a temperature variation to obtain a first estimated piezoresistance, and using the first estimated piezoresistance and the first and the second relations to compensate the second piezoresistance for the thermal effect.

3. A system according to claim 2, wherein:
the temperature variation is present in reference to a second variable temperature;
the first and the second variable temperatures are a first environmental temperature and a second environmental temperature of the microcantilever, respectively;
the first variable temperature has a temperature domain;
the second variable temperature varies in the temperature domain;
the system is a thermal-effect self-compensating system;
the first relation is characterized as a first temperature piezoresistance function of the first variable temperature;
the second relation is characterized as a second temperature piezoresistance function of the first variable temperature;
the system estimates the temperature variation according to the first estimated piezoresistance and the first temperature piezoresistance function to obtain an estimated environmental temperature;
the system obtains a second estimated piezoresistance according to the estimated environmental temperature and the second temperature piezoresistance function, and converts the second estimated piezoresistance into a first signal; and
the system measures the second piezoresistance at the temperature variation to produce a second signal, and uses the first signal to compensate the second signal for the temperature variation, thereby compensating the second piezoresistance for the thermal effect.

4. A system according to claim 3, wherein the first piezoresistor further has a resistance temperature coefficient effect, and the first temperature piezoresistance function is only associated with the resistance temperature coefficient effect.

5. A system according to claim 3, wherein the thermal effect of the microcantilever has a resistance temperature coefficient effect and a bimorph effect, and the second temperature piezoresistance function is associated with the resistance temperature coefficient and the bimorph effects.

6. A system according to claim 1, wherein:
the substrate structure further includes a reference structure integrated into the substrate structure; and
the reference structure includes the first piezoresistor further having a first resistance temperature coefficient effect, and the first piezoresistance is only affected by the first resistance temperature coefficient effect.

7. A system according to claim 6, wherein the reference structure serves as a thermometer.

8. A system according to claim 6, wherein:
the microcantilever has a sensing piezoresistor and a bimorph effect; and
the sensing piezoresistor has the second piezoresistance and a second resistance temperature coefficient effect, and the second piezoresistance is affected by the second resistance temperature coefficient and the bimorph effects.

9. A system according to claim 8, wherein the microcantilever is structured by referring to the reference structure, and each of the first and the sensing piezoresistors is made of a first material having a piezoresistive property.

10. A system according to claim 9, wherein the first material includes a semiconductor material being one of a polycrystalline silicon and a monocrystalline silicon.

11. A system according to claim 1, wherein the microcantilever is made of a multilayer composite material.

12. A system according to claim 11, wherein the multilayer composite material includes a layer made of a semiconductor material being one of a polycrystalline silicon and a monocrystalline silicon.

13. A method for compensating a thermal effect, comprising steps of:
(a) measuring a first piezoresistance of a first object affected by a specific temperature variation of a first variable temperature to measure the first variable temperature for obtaining an estimated temperature;
(b) obtaining a first estimated piezoresistance according to the estimated temperature;
(c) measuring a second piezoresistance of a second object affected by the specific temperature variation to obtain a second estimated piezoresistance; and
(d) compensating the thermal effect of the second object due to the specific temperature variation by using a difference between the first and the second estimated piezoresistances.

14. A method according to claim 13, before the step (a) further comprising steps of:

(a1) providing a substrate structure, wherein the substrate structure includes the first object being a first piezoresistor, and the first piezoresistor is buried in the substrate structure and has the first piezoresistance;

(a2) providing the second object being a microcantilever having the second piezoresistance and the thermal effect, wherein the second object sticks out from the substrate structure; and (a3) measuring the first and the second piezoresistances according to a second variable temperature to respectively determine a first temperature piezoresistance function and a second temperature piezoresistance function, both of which are associated with the second variable temperature.

15. A method according to claim 14, wherein:

the step (a3) is performed when the first piezoresistor and the microcantilever are operated in a calibration state;

the steps (a), (b), (c) and (d) are performed when the first piezoresistor and the microcantilever are operated in a sensing state;

the specific temperature variation is present in reference to the first variable temperature;

the first and the second variable temperatures are a first environmental temperature and a second environmental temperature of the microcantilever, respectively;

the estimated temperature is an estimated environmental temperature;

the first and the second variable temperatures have a same temperature domain;

in the step (a), the first piezoresistance of the first object affected by the specific temperature variation is measured to obtain a third estimated piezoresistance;

the estimated environmental temperature is obtained according to the third estimated piezoresistance and the first temperature piezoresistance function; and the first estimated piezoresistance is obtained further according to the second temperature piezoresistance function.

16. A method according to claim 14, further comprising steps of:

converting the first estimated piezoresistance into a first signal;

measuring the second piezoresistance of the second object affected by the specific temperature variation to produce a second signal; and compensating the second signal for the specific temperature variation by using the first signal, thereby compensating the second piezoresistance for the thermal effect.

17. A thermal-effect compensating apparatus, comprising:

a substrate structure including a first piezoresistor buried in the substrate structure; and a microcantilever formed on the substrate structure.

18. A thermal-effect compensating apparatus according to claim 17, being a thermal-effect self-compensating apparatus, wherein:

the substrate structure further includes a reference structure integrated into the substrate structure;

the reference structure includes the first piezoresistor having a piezoresistance and a resistance temperature coefficient effect; and the piezoresistance is only affected by the resistance temperature coefficient effect.

19. A thermal-effect compensating apparatus according to claim 18, wherein the reference structure serves as a thermometer.

20. A thermal-effect compensating apparatus according to claim 17, wherein:

the microcantilever has a sensing piezoresistor and a bimorph effect; and the sensing piezoresistor has a piezoresistance and a resistance temperature coefficient effect, and the piezoresistance is affected by the resistance temperature coefficient and the bimorph effects.

* * * * *